United States Patent [19]

Bishop et al.

[11] Patent Number: 5,093,026
[45] Date of Patent: Mar. 3, 1992

[54] BIPHENYLYLETHANES

[75] Inventors: David I. Bishop, Creekmoor; Stephen Lewis, Southbourne; David Coates, Merley; Simon Greenfield, Creekmoor, all of Great Britain; Eike Poetsch, Mühltal, Fed. Rep. of Germany; Volker Meyer, Groβ-Zimmern, Fed. Rep. of Germany; Klaus P. Stahl, Darmstadt, Fed. Rep. of Germany; Volker Reiffenrath, Rossdorf, Fed. Rep. of Germany; Herbert Plach, Darmstadt, Fed. Rep. of Germany; Reinhard Hittich, Modautal, Fed. Rep. of Germany; Andreas Wächtler, Griesheim, Fed. Rep. of Germany

[73] Assignee: Merck Patent Gesellschaft Mit Beschrankter Haftung, Darmstadt, Fed. Rep. of Germany

[21] Appl. No.: 469,498

[22] PCT Filed: Jan. 22, 1990

[86] PCT No.: PCT/EP90/00119
§ 371 Date: Apr. 2, 1990
§ 102(e) Date: Apr. 2, 1990

[87] PCT Pub. No.: WO90/08756
PCT Pub. Date: Aug. 9, 1990

[30] Foreign Application Priority Data

Jan. 27, 1989 [DE] Fed. Rep. of Germany ....... 3902327
Apr. 21, 1989 [DE] Fed. Rep. of Germany ....... 3913164

[51] Int. Cl.$^5$ .................. C09K 19/30; C09K 19/52; C09K 19/12; C09K 19/06
[52] U.S. Cl. .................. 252/299.63; 252/299.01; 252/299.6; 252/299.636; 359/103
[58] Field of Search .......... 252/299.01, 299.6, 299.62, 252/299.63, 299.64, 299.65, 299.66, 299.67; 350/350 R

[56] References Cited

U.S. PATENT DOCUMENTS

| 4,621,091 | 11/1986 | Petrzilka et al. | 450/350 R |
| 4,709,030 | 11/1987 | Petzilka et al. | 544/242 |
| 4,808,333 | 2/1989 | Hugnh-ba et al. | 252/299.66 |
| 4,911,863 | 3/1990 | Sage et al. | 252/299.65 |

FOREIGN PATENT DOCUMENTS

| 0181601 | 5/1986 | European Pat. Off. |
| 2216523 | 10/1989 | United Kingdom. |
| 8903416 | 4/1989 | World Int. Prop. O. |

Primary Examiner—Robert L. Stoll
Assistant Examiner—Shean C. Wu
Attorney, Agent, or Firm—Millen, White & Zelano

[57] ABSTRACT

Biphenylylethanes of the formula I, $$R^1-CH_2-X-(CH_2CH_2)_m-Ph-Ph-CH_2CH_2-Ph-Y-CH_2-R^2 \quad \text{I}$$

in which
R$^1$ and R$^2$ are each, independently of one another, alkyl, alkenyl or oxaalkyl having up to 12 C atoms, and one of the radicals R$^1$ and R$^2$ is alternatively H,
m is 0 or 1,
X and Y are each, independently of one another, O, S, CO—O, O—CO, O—CO—O or a single bond, the radical X is alternatively 1,4-phenylene or trans-1,4-cyclohexylene, and the radical Y is alternatively trans-1,4-cyclohexylene, and
is 1,4-phenylene, and one or two of the radicals Ph is alternatively 2- or 3-fluoro-1,4-phenylene, with the proviso that, in the case (a) where X=1,4-phenylene and m=1, one or two of the radicals Ph are 2- or 3-fluoro-1,4-phenylene, and (b) in the case where X=trans-1,4-cyclohexylene, m=0 and one or two of the radicals Ph are 2- or 3-fluoro-1,4-phenylene, are suitable as components of liquid-crystalline phases.

2 Claims, No Drawings

BIPHENYLYLETHANES

The invention relates to biphenylylethanes of the formula I,

R¹—CH₂—X—(CH₂CH₂)ₘ—Ph—Ph—CH₂C-
H₂—Ph—Y—CH₂—R²    I in which
- R¹ and R² are each, independently of one another, alkyl, alkenyl or oxaalkyl having up to 12 C atoms, and one of the radicals R¹ and R² is alternatively H,
- m is 0 or 1,
- X and Y are each, independently of one another, O, S, CO—O, O—CO, O—CO—O or a single bond, the radical X is alternatively 1,4-phenylene or trans-1,4-cyclohexylene, and the radical Y is alternatively trans-1,4-cyclohexylene, and
- Ph is 1,4-phenylene, and one or two of the radicals Ph is alternatively 2- or 3-fluoro-1,4-phenylene, with the proviso that, in the case (a) where X=1,4-phenylene and m=1, one or two of the radicals Ph 2-or 3-fluoro-1,4-phenylene, and (b) in the case where X=trans-1,4-cyclohexylene, m=0 and one or two of the radicals Ph 2- or 3-fluoro-1,4-phenylene.

The compounds of the formula I can be used as components of liquid-crystalline phases, in particular for the displays based on the principle of the twisted cell, the guest/host effect, the effect of deformation of lined phases or the effect of dynamic scattering.

Compounds of the formula I are preferably also suitable for use as components in liquid-crystalline phases for displays based on the ECB effect.

Similarly liquid-crystalline compounds are known, for example, from U.S. Pat. No. 4,695,131. However, the compounds described therein contain a cyclohexylethyl group.

Chiral compounds for ferroelectric liquid-crystal mixtures of the formula

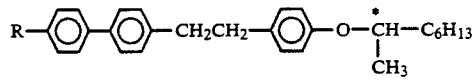

are described in JP 61/243,037-A. In addition, a chiral compound of the structure

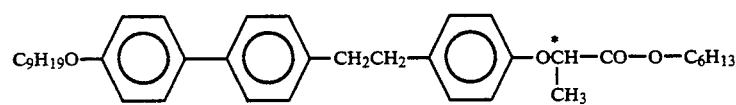

is described in EP-OS 0,259,995.
A compound of the structure

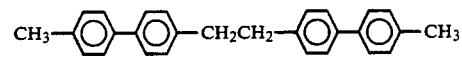

in the synthesis of cyclophan compounds is reported by H. A. Staab and M Haenel (Chem. Ber., 106 (7), 2150-2202 (1973)).

Finally, G. W. Gray et al. in Liquid Crystals, 1986, Vol. 1, No. 5, pp. 407-413, report, inter alia, on compounds of the formula

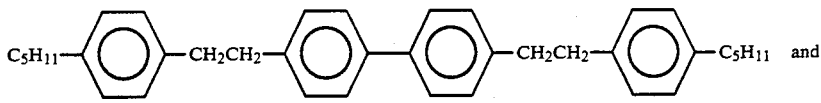

in this connection, indicate a negative effect, generally accepted by specialists in the liquid-crystal field, of separation of the π systems in this connection.

The invention had the object of finding novel, stable, liquid-crystalline or mesogenic compounds having high birefringence which are suitable as components of liquid-crystalline phases having low viscosity, high nematogeneity and favourable low-temperature behaviour. This object has been achieved by the provision of the compounds of the formula I.

It has been found that the compounds of the formula I are preeminently suitable as components of liquid-crystalline phases. In particular, they can be used to prepare stable, liquid-crystalline phases having relatively high optical anisotropy and positive or negative dielectric anisotropy. The substances of the formula I are particularly preferably suitable, for example, for use in mixtures for ECB effects.

The ECB effect (electrically controlled birefringence) or alternatively the DAP effect (deformation of aligned phases) was described for the first time in 1971 (M. F. Schieckel and K. Fahrenschon, "Deformation of nematic liquid crystals with vertical orientation in electrical fields", Appl. Phys. Lett. 19 (1971), 3912). This is followed by papers by J. F. Kahn (Appl. Phys. Lett. 20 (1972), 1193) and G. Labrunie and J. Robert (J. Appl. Phys. 44 (1973), 4869).

The papers by J. Robert and F. Clerc (SID 80 Digest Techn. Papers (1980), 30), J. Duchene (Displays 7 (1986), 3) and H. Schad (SID 82 Digest Techn. Papers (1982), 244) have shown that liquid-crystalline phases must have high values for the ratio between the elastic constants $K_3/K_1$, high values for the optical anisotropy $\Delta n$ and negative values for the dielectric anisotropy $\Delta\epsilon$ in order that they can be employed for high-information display elements based on the ECB effect.

Electro-optical display elements based on the ECB effect have a homeotropic edge orientation, i.e. the liquid-crystalline phase has negative dielectric anisotropy.

Surprisingly, it has been shown that the addition of compounds of the formula I gives liquid-crystalline phases which meet all the abovementioned criteria in an excellent manner.

In addition, the provision of the compounds of the formula I very generally considerably broadens the range of liquid-crystalline substances which are suitable, from various applicational points of view, for the preparation of nematic mixtures.

The compounds of the formula I have a broad field of application. Depending on the choice of substituents, these compounds can be used as base materials from which liquid-crystalline phases are predominantly composed; however, it is also possible to add compounds of the formula I to liquid-crystalline base materials from other classes of compounds, in order, for example, to optimize the dielectric and/or optical anisotropy of a dielectric of this type. The compounds of the formula I are furthermore suitable as intermediates for the preparation of other substances which can be used as components of liquid-crystalline phases.

In the pure state, the compounds of the formula I are colourless and form liquid-crystalline mesophases in a temperature range which is favourable for electro-optical use. They are very stable chemically, thermally and to light.

The invention thus relates to the compounds of the formula I and to the use of these compounds as components of liquid-crystalline phases. The invention furthermore relates to liquid-crystalline phases containing at least one compound of the formula I, and to liquid-crystal display elements which contain such phases.

Above and below, $R^1$, $R^2$, X, Y and Ph have the meaning stated, unless expressly stated otherwise.

If $R^1$ and/or $R^2$ are alkyl radicals in which, in addition, one ("oxaalkyl") $CH_2$ group may be replaced by O atoms, they may be straight-chain or branched. They are preferably straight-chain, have 2, 3, 4, 5, 6 or 7 C atoms and accordingly are preferably ethyl, propyl, butyl, pentyl, hexyl, heptyl, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, furthermore methyl, octyl, nonyl, decyl, undecyl, dodecyl, tridecyl, tetradecyl, pentadecyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl. The radicals $R^1$-X and/or $R^2$-Y in which X and Y are O are thus an alkoxy or alkoxyalkoxy radical having 2, 3, 4, 5, 6 or 7 C atoms. Accordingly, they are preferably ethoxy, propoxy, butoxy, pentoxy, hexoxy, heptoxy, methoxy, octoxy, nonoxy, decoxy, undecoxy, dodecoxy, tridecoxy, tetradecoxy, pentadecoxy, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, or 1,3-, 1,4-, 1,5-, 1,6-, 2,4-, 2,5-, 2,6-, 3,5-,3,6- or 4,6-dioxaheptyl.

Particularly preferred alkyl radicals are also those in which one $CH_2$ group has been replaced by a —CH=CH— group or by —CHF—.

Compounds of the formula I having branched wing groups $R^1$or $R^2$may occasionally be of importance due to better solubility in the customary liquid-crystalline base materials, but in particular as chiral dopes if they are optically active.

Branched groups of this type generally contain not more than one chain branch. Preferred branched radical [sic] are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-methyl-3-oxapentyl or 2-methyl-3-oxahexyl.

In the case of compounds having branched wing groups, the formula I covers both the optical antipodes and the racemates, and mixtures thereof.

The preferred meanings of X and Y are O or a single bond, the single bond being particularly preferred. Particularly preferred compounds are those in which one of the radicals Ph is 2- or 3-fluoro-1,4-phenylene. The radicals $R^1$—X and $R^2$—Y are preferably straight-chain alkyl or alkoxy.

Of the compounds of the formula I and their subformulae, those are preferred in which at least one of the radicals present therein has one of the preferred meanings indicated.

Particularly preferred smaller groups of compounds according to the invention are those of the subformulae below:

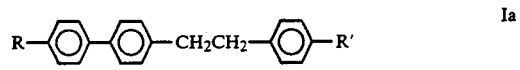   Ia

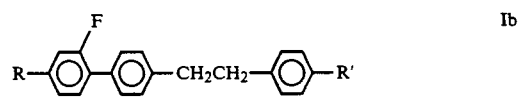   Ib

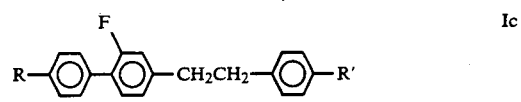   Ic

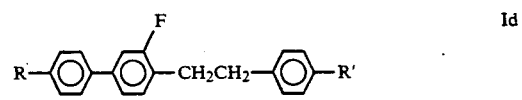   Id

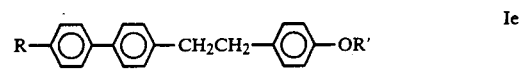   Ie

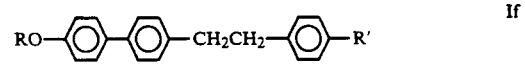   If

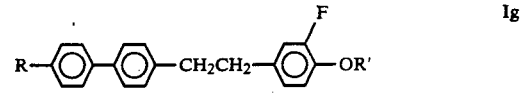   Ig

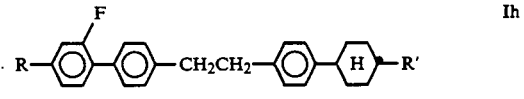   Ih

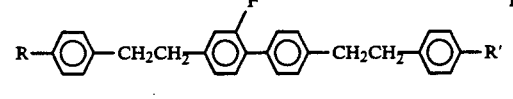   Ii

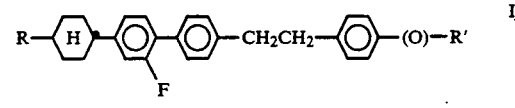   Ij

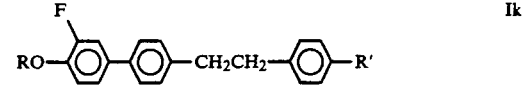   Ik

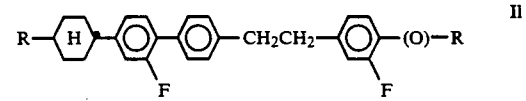   Il (O) is O or a single bond.

R and R' are each n-alkyl having up to 12 C atoms.

The central part of the compounds according to the invention —Ph—Phe—CH₂CH₂—Ph— preferably has one of the following meanings:

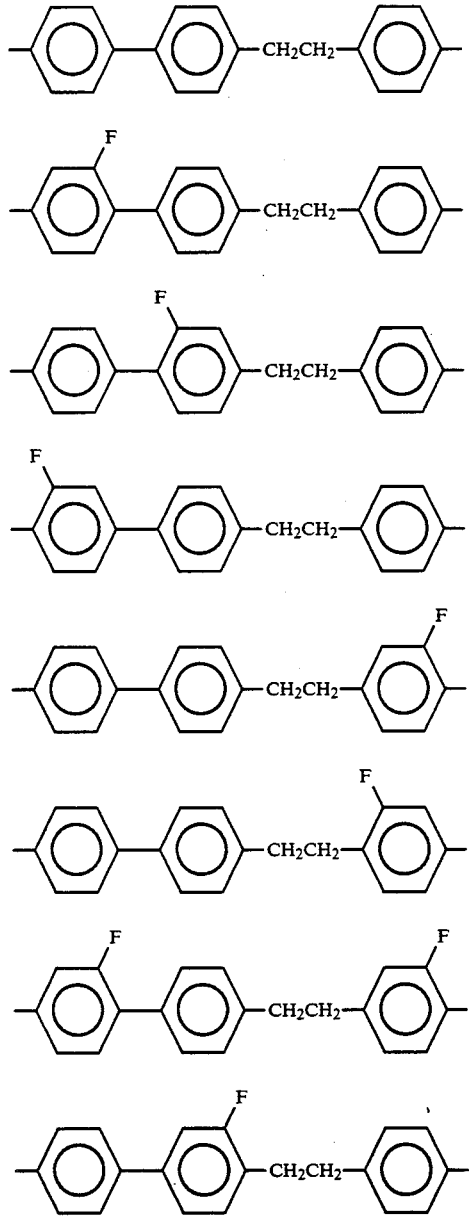

Meaning 2 is particularly preferred.

Particularly preferred biphenylylethanes are those of the formula II

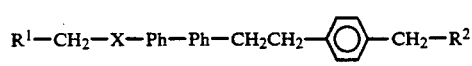

in which R¹ and R² have the meaning indicated in claim 1, X is O or a single bond, one of the radicals Ph is 2- or 3-fluoro-1,4-phenylene, and the other radical Ph is 1,4-phenylene, and biphenylylethanes of the formula IIa

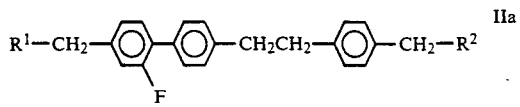

in which R¹ and R² have the meaning indicated in claim 1.

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. At the same time, use may also be made of variants which are known per se, but are not described here in greater detail.

If desired, the starting materials can also be formed in situ by not isolating them from the reaction mixture, but instead immediately reacting them further to form the compounds of the formula I.

Thus, the compounds of the formula I can be prepared by catalytically hydrogenating a compound of the formula II or a corresponding ethyne compound

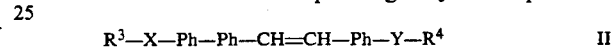

under conditions which are known to those skilled in the art. In the formula II, X, Y and Ph have the meanings indicated above. R³ and R are each, independently of one another, alkyl or oxaalkyl.

The compounds of the formula II can be obtained in a manner known per se by the method of Wittig or by Heck coupling from appropriate styrene compounds using haloaromatics, which are either known or can be prepared entirely analogously to known compounds.

Ethynes of the formula II can also be prepared by coupling alkynylzin [sic] compounds with aryl halides analogously to the process described by A. O. King, E. Negishi, F. J. Villani and A. Silveira in J. Org. Chem. 43 (1978) 358.

Ethynes of the formula II can also be prepared via the Fritsch-Buttenberg-Wiechell rearrangement (Ann. 279, 319, 327, 332, 1984), in which the 1,1-diaryl-2-haloethylenes are rearranged in the presence of strong bases to form diarylacetylenes.

Ethynes of the formula II can furthermore be prepared from 4-substituted phenyl- or cyclohexylacetylenes and aryl halides in the presence of a palladium catalyst, for example bis(triphenylphosphine)palladium-(II) chloride, and copper(I) iodide (described in Synthesis (1980) 627 or Tetrahedron Letters 27 (1986) 1171).

Compounds according to the invention containing alkenyl groups can be prepared analogously to similar, known compounds by the Wittig reaction, the starting materials (conforming to the formula I, but one of the radicals R¹ and R² is —(CH₂)ₓ—CHO or, for example, —(CH₂)ₓ—Br, X=0 to 5) being accessible analogously to the methods described above.

The compounds of the formula I can furthermore be prepared by cross-coupling in accordance with DOS 3,608,502, DOS 3,632,410 or DOS 3,736,489 or by Wolff-Kishner reduction of appropriate methylene ketones, which are themselves accessible from the corresponding arylacetyl chlorides and corresponding benzene or biphenyl precursors.

The liquid-crystalline phases according to the invention comprise 2 to 15, preferably 3 to 12, components, including at least one compound of the formula I. The other components are preferably selected from nematic or nematogenic substances, in particular known substances from the classes of the azoxybenzenes, benzylideneanilines, biphenyls, terphenyls, phenyl or cyclohexyl benzoates, phenyl or cyclohexyl esters of cyclohexanecarboxylic acid, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclophexylpyrimidines [sic], phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, and substituted cinnamic acids.

The most important compounds which are suitable as components of liquid-crystalline phases of this type may be characterized by the formula IV $$R^6\text{—}L\text{—}G\text{—}E\text{—}R^7 \qquad \text{IV}$$

in which L and E are each a carbocyclic or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene and tetrahydronaphthalene, quinazoline and tetrahydroquinazoline,

| G is | —CH=CH— | —N(O)=N— |
|---|---|---|
| | —CH=CY— | —CH=N(O)— |
| | —C≡C— | —CH$_2$—CH$_2$— |
| | —CO—O— | —CH$_2$—O— |
| | —CO—S— | —CH$_2$—S— |
| | —CH=N— | —COO—Phe—COO— | or a C—C single bond,

Y is halogen, preferably chlorine, or —CN, and $R^6$ and $R^7$ are alkyl, alkoxy, alkanoyloxy or alkoxycarbonyloxy having up to 18, preferably up to 8 carbon atoms, or one of these radicals [lacuna] by CN, NC, NO$_2$, CF$_3$, F, Cl or Br.

In most of these compounds, $R^6$ and $R^7$ are different from one another, one of these radicals usually being an alkyl or alkoxy group. Other variants of the proposed substituents are also customary. Many such substances, or alternatively mixtures thereof, are commercially available. All these substances can be obtained by methods known from the literature.

The phases according to the invention contain about 0.1 to 99, preferably 10 to 95%, of one or more compounds of the formula I. Furthermore preferred are liquid-crystalline phases according to the invention containing 0.1–40, preferably 0.5–30%, of one or more compounds of the formula I.

The compounds of the formula I can also be used as components of smectic or chirally [sic] tilted smectic liquid-crystalline phases. These phases are preferably chirally [sic] tilted smectic liquid-crystalline phases whose achiral base mixture contains, besides compounds of the formula I, at least one other component having negative or a small value of positive dielectric anisotropy. This (these) further component(s) of the achiral base mixture can make up 1 to 50%, preferably 10 to 25%, of the base mixture.

The phases according to the invention are prepared in a manner which is customary per se. In general, the components are dissolved in one another, expediently at elevated temperature.

By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature. For example, conductive salts, preferably ethyldimethyldodecylammonium 4-hexyloxybenzoate, tetrabutylammonium tetraphenylborate or complex salts of crown ethers (cf. for example, I. Haller et al., Mol. Cryst. Liq. Cryst. Volume 24, Pages 249–258 (1973)) can be added to improve the conductivity, dichroic dyes can be added for the production of coloured guest-host systems, or substances can be added to modify the dielectric anisotropy, the viscosity and/or the orientation of the nematic phases. Substances of this type are described, for example, in DE-OS 2,209,127, 2,240,864, 2,321,632, 2,338,281, 2,450,088, 2,637,430, 2,853,728 and 2,902,177.

The examples below are intended to illustrate the invention without representing a limitation. mp.=melting point, cp.=clear point. Above and below, percentages are per cent by weight; all temperatures are indicated in degrees Celsius. "Customary work-up" means that water is added, the mixture is extracted with methylene chloride, the organic phase is separated off dried and evaporated and the product is purified by crystallization and/or chromatography.

EXAMPLE 1

A solution of 10.6 g of 1-(p-ethoxyphenyl)-2-(4'-n-pentylbiphenyl-4-yl)ethene [obtained by Heck coupling of 4-ethoxystyrene with 4-bromo-4'-n-pentylbiphenyl] in 200 ml of tetrahydrofuran is hydrogenated in the presence of Pd/C until the take-up of H is complete. Customary work-up gives 1-(p-ethoxyphenyl)-2-(4'-n-pentylbiphenyl-4-yl)ethane, mp. 81°, cp. 145°.

The following are prepared analogously:

1-(p-methylphenyl)-2-(4'-n-propylbiphenyl-4-yl)ethane, mp. 116°

1-(p-ethoxyphenyl)-2-(4'-ethylbiphenyl-4-yl)ethane, mp. 114°, cp. 136.5°

1-(p-propylphenyl)-2-(4'-ethylbiphenyl-4-yl)ethane, mp. 77°, cp. 121°

1-(p-propylphenyl)-2-(4'-pentylbiphenyl-4-yl)-ethane, mp. 57°, cp. 138°

1-(p-ethoxyphenyl)-2-(4'-butoxybiphenyl-4-yl)ethane, mp. 133°, cp. 176°

1-(p-methoxyphenyl)-2-(4'-pentylbiphenyl-4-yl)ethane, mp. 111°, cp. 131°

1-(p-ethoxyphenyl)-2-(4'-propylbiphenyl-4-yl)ethane, mp. 94°, cp. 148°

1-(p-butoxyphenyl)-2-(4'-pentylbiphenyl-4-yl)ethane, mp. 158°

EXAMPLE 2

A solution of 1.9 g of 1-(p-ethoxyphenyl)-2-[4'-(trans-4-n-pentylcyclohexyl)-3'-fluorobiphenyl-4-yl]ethene [obtained by Heck coupling of 4-ethoxystyrene with 4'-(trans-4-n-pentylcyclohexyl)-3'-fluoro-4-bromobiphenyl] in 50 ml of tetrahydrofuran is hydrogenated in the presence of Pd/C. Customary work-up gives 1-(p-ethoxyphenyl)-2-[4'-(trans-4-n-pentylcyclohexyl)-3'-fluorobiphenyl-4-yl)ethane.

The following is prepared analogously:

1-(p-ethoxyphenyl)-2-(4'-ethoxy'3'-fluoro-biphenyl-4-yl)-ethane, mp. 133°, cp. 155°

EXAMPLE 3

A solution of 3.2 g of 1-(p-ethylphenyl)-2-[4'-(trans-4-n-pentylcyclohexyl)-2'-fluorobiphenyl-4-yl]ethene [obtained by Heck coupling of p-ethylstyrene with 4'-(trans-4-n-pentylcyclohexyl)-2'-fluoro-4-bromobiphenyl] in 100 ml of tetrahydrofuran is hydrogenated in the presence of Pd/C. Customary work-up gives 1-(p-ethylphenyl)-2-[4'-(trans-4-n-pentylcyclohexyl)-2'-fluorobiphenyl-4-yl)ethane.

The following are prepared analogously:

1-(p-methylphenyl)-2-[4'-(trans-4-ethylcyclohexyl)-2'-fluorobiphenyl-4-yl)ethane
1-(p-ethylphenyl)-2-[4'(trans-4-ethylcyclohexyl)-2'-fluorobiphenyl-4-yl)ethane
1-(p-propylphenyl)-2-[4'-(trans-4-ethylcyclohexyl)-2'-fluorobiphenyl-4-yl)ethane
1-(p-pentylphenyl)-2-[4'-(trans-4-ethylcyclohexyl)-2'-fluorobiphenyl-4-yl)ethane
1-(p-methylphenyl)-2-[4'-(trans-4-propylcyclohexyl)-2'-fluorobiphenyl-4-yl)ethane
1-(p-ethylphenyl)-2-[4'-(trans-4-propylcyclohexyl)-2'-fluorobiphenyl-4-yl)ethane
1-(p-propylphenyl)-2-(4'-(trans-4-propylcyclohexyl)-2'-fluorobiphenyl-4-yl)ethane
1-(p-pentylphenyl)-2-[4'- trans-4-propylcyclohexyl)-2'-fluorobiphenyl-4-yl)ethane
1-(p-methylphenyl)-b 2-[4'-(trans-4-butylcyclohexyl)-2'-fluorobiphenyl-4-yl)ethane
1-(p-ethylphenyl)-2-[4'-(trans-4-butylcyclohexyl)-2'-fluorobiphenyl-4-yl)ethane
1-(p-propylphenyl)-2-[4'-(trans-4-butylcyclohexyl)-2'-fluorobiphenyl-4-yl)ethane
1-(p-pentylphenyl)-2-[4'-(trans-4-butylcyclohexyl)-2'-fluorobiphenyl-4-yl)ethane
1-(p-methylphenyl)-2-[4'-(trans-4-pentylcyclohexyl)-2'-fluorobiphenyl-4-yl)ethane
1-(p-propylphenyl)-2-[4'-(trans-4-pentylcyclohexyl)-2'-fluorobiphenyl-4-yl)ethane
1-(p-butylphenyl)-2-[4'-(trans-4-pentylcyclohexyl)-2'-fluorobiphenyl-4-yl)ethane
1-(p-pentylphenyl)-2-[4'-(trans-4-pentylcyclohexyl)-2'-fluorobiphenyl-4-yl)ethane
1-(p-ethoxyphenyl)-2-[4'(trans-4-pentylcyclohexyl)-2'-fluorobiphenyl-4-yl)ethane, mp. 69°, cp. 229.4°

EXAMPLE 4

A solution of 1.2 g of 1-(p-ethylphenyl)-2-[4'-pentyl-2'-fluorobiphenyl-4-yl]ethene [obtained by Heck coupling of p-ethyl styrene with 4'-n-pentyl-2'-fluoro-4-bromobiphenyl] in 50 ml of tetrahydrofuran is hydrogenated in the presence of Pd/C. Customary work-up gives 1-(p-ethylphenyl)-2-(4'-n-pentyl-2'-fluorobiphenyl-4-yl)ethane.

The following are prepared analogously:

1-(p-ethylphenyl)-2-(4'-ethyl-2'-fluorobiphenyl-4-yl)ethane
1-(p-ethylphenyl)2-(4'-propyl-2'-fluorobiphenyl-4-yl)ethane
1-(p-ethylphenyl)-2-(4'-butyl-2'-fluorobiphenyl-4-yl)ethane
1-(p-ethylphenyl)-2-(4'-heptyl-2'-fluorobiphenyl-4-yl)ethane
1-(p-methylphenyl)-2-(4'-ethyl-2'-fluorobiphenyl-4-yl)ethane
1-(p-methylphenyl)-2-(4'-propyl-2'-fluorobiphenyl-4-yl)ethane, mp. 65°, cp. 66.3°
1-(p-methylphenyl)-2-(4'-butyl-2'-fluorobiphenyl-4-yl)ethane
1-(p-methylphenyl)-2-(4'-pentyl-2'-fluorobiphenyl-4-yl)ethane, mp. 41°, cp. 67.4°
1-(p-methylphenyl)-2-(4'-heptyl-2'-fluorobiphenyl-4-yl)ethane
1-(p-methoxyphenyl)-2-(4'-ethyl-2'-fluorobiphenyl-4-yl)ethane
1-(p-methoxyphenyl)-2-(4'-propyl-2'-fluorobiphenyl-4-yl)ethane
1-(p-methoxyphenyl)-2-(4'-butyl-2'-fluorobiphenyl-4-yl)ethane
1-(p-methoxyphenyl)-2-(4'-pentyl-2'-fluorobiphenyl-4-yl)ethane, mp. 49°, cp. 87.5°
1-(p-methoxyphenyl)-2-(4'-heptyl-2'-fluorobiphenyl-4-yl)ethane
1-(p-propylphenyl)-2-(4'-ethyl-2'-fluorobiphenyl-4-yl)ethane, mp. 57°
1-(p-propylphenyl)-2-(4'-propyl-2'-fluorobiphenyl-4-yl)ethane, mp. 52°, cp. 60°
1-(p-propylphenyl)-2-(4'-butyl-2'-fluorobiphenyl-4-yl)ethane
1-(p-propylphenyl)-2-(4'-pentyl-2'-fluorobiphenyl-4-yl)ethane mp. 37°, cp. 67.5°
1-(p-propylphenyl)-2-(4'-heptyl-2'-fluorobiphenyl-4-yl)ethane
1-(p-butylphenyl)-2-(4'-ethyl-2'-fluorobiphenyl-4-yl)ethane
1-(p-butylphenyl)-2-(4'-propyl-2'-fluorobiphenyl-4-yl)ethane
1-(p-butylphenyl)-2-(4'-butyl-2'-fluorobiphenyl-4-yl)ethane
1-(p-butylphenyl)-2-(4'-pentyl-2'-fluorobiphenyl-4-yl)ethane
1-(p-butylphenyl)-2-(4'-heptyl-2'-fluorobiphenyl-4-yl)ethane
1-(p-pentylphenyl)-2-(4'-ethyl-2'-fluorobiphenyl-4-yl)ethane
1-(p-pentylphenyl)-2-(4'-propyl-2'-fluorobiphenyl-4-yl)ethane, mp. 40°, cp. 67.7°
1-(p-pentylphenyl)-2-(4'-butyl-2'-fluorobiphenyl-4-yl)ethane
1-(p-pentylphenyl)-2-(4'-pentyl-2'-fluorobiphenyl-4-yl)ethane
1-(p-pentylphenyl)-2-(4'-heptyl-2'-fluorobiphenyl-4-yl)ethane
1-(p-heptylphenyl)-2-(4'-ethyl-2'-fluorobiphenyl-4-yl)ethane
1-(p-heptylphenyl)-2-(4'-propyl-2'-fluorobiphenyl-4-yl)ethane
1-(p-heptylphenyl)-2-(4'-butyl-2'-fluorobiphenyl-4-yl)ethane
1-(p-heptylphenyl)-2-(4'-pentyl-2'-fluorobiphenyl-4-yl)ethane
1-(p-heptylphenyl)-2-4(4'-heptyl-2'-fluorobiphenyl-4-yl)ethane
1-(p-propylphenyl)-2-(4'-ethyl-2-fluorobiphenyl-4-yl)ethane
1-(p-propylphenyl)-2-(4'-propyl-2-fluorobiphenyl-4-yl)ethane
1-(p-propylphenyl)-2-(4'-butyl-2-fluorobiphenyl-4-yl)ethane
1-(p-propylphenyl)-2-(4'-pentyl-2-fluorobiphenyl-4yl)ethane
1-(p-propylphenyl)-2-(4'-heptyl-2-fluorobiphenyl-4-yl)ethane 1-(p-propylphenyl)-2-(4'-propoxy-2-fluorobiphenyl-4-yl)ethane
1-(p-pentylphenyl)-2-(4'-ethyl-2-fluorobiphenyl-4-yl)ethane
1-(p-pentylphenyl)-2-(4'-propyl-2-fluorobiphenyl-4-yl)ethane
1-(p-pentylphenyl)-2-(4'-butyl-2-fluorobiphenyl-4-yl)ethane
1-(p-pentylphenyl)-2-(4'-pentyl-2-fluorobiphenyl-4-yl)ethane
1-(p-pentylphenyl)-2-(4'-heptyl-2-fluorobiphenyl-4-yl)ethane
1-(p-pentylphenyl)-2-(4'-propoxy-2-fluorobiphenyl-4-yl(ethane
1-(p-methoxyphenyl)-2-(4'-ethyl-2-fluorobiphenyl-4-yl)ethane
1-(p-methoxyphenyl)-2-(4'-propyl-2-fluorobiphenyl-4-yl)ethane
1-(p-methoxyphenyl)-2-(4'-butyl-2-fluorobiphenyl-4-yl)ethane
1-(p-methoxyphenyl)-2-(4'-pentyl-2-fluorobiphenyl-4-yl)ethane
1-(p-methoxyphenyl)-2-(4'-heptyl-2-fluorobiphenyl-4-yl)ethane
1-(p-methoxyphenyl)-2-(4'-propoxy-2-fluorobiphenyl-4-yl)ethane
1-(p-propylphenyl)-2-(4'-ethyl-3-fluorobiphenyl-4-yl)ethane
1-(p-propylphenyl)-2-(4'-propyl-3-fluorobiphenyl-4-yl)ethane
1-(p-propylphenyl)-2-(4'-pentyl-3-fluorobiphenyl-4-yl)ethane
1-(p-propylphenyl)-2-(4'-heptyl-3-fluorobiphenyl-4-yl)ethane
1-(p-propylphenyl)-2-(4'-propoxy-3-fluorobiphenyl-4-yl)ethane
1-(p-methoxyphenyl)-2-(4'-ethyl-3-fluorobiphenyl-4-yl)ethane
1-(p-methoxyphenyl)-2-(4'-propyl-3-fluorobiphenyl-4-yl)ethane
1-(p-methoxyphenyl)-2-(4'-pentyl-3-fluorobiphenyl-4-yl)ethane
1-(p-methoxyphenyl)-2-(4'-heptyl-3-fluorobiphenyl-4-yl)ethane
1-(p-methoxyphenyl)-2-(4'-propoxy-3-fluorobiphenyl-4-yl)ethane
1-(p-propylphenyl)-2-(4'-ethoxy-2'-fluorobiphenyl-4-yl)ethane
1-(2-fluoro-4-propylphenyl)-2-(4'-ethylbiphenyl-4-yl)ethane
1-(2-fluoro-4-propylphenyl)-2-(4'-propylbiphenyl-4-yl)ethane
1-(2-fluoro-4-propylphenyl)-2-(4'-butylbiphenyl-4-yl)ethane
1-(2-fluoro-4-propylphenyl)-2-(4'-pentylbiphenyl-4-yl)ethane
4,4-bis-(p-propylphenylethyl)-2-fluorobiphenyl
4,4-bis-(p-ethylphenylethyl)-2-fluorobiphenyl
4,4-bis-(p-butylphenylethyl)-2-fluorobiphenyl
4,4-bis-(p-pentylphenylethyl)-2-fluorobiphenyl

We claim:

1. A liquid crystalline mixture containing at least one compound of the formula

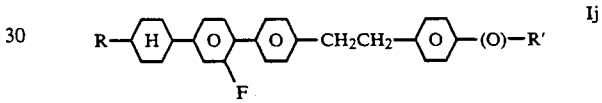

in which
R and R' are each an alkyl having up to 12 carbon atoms.

2. A liquid crystal display element which contains a liquid crystalline mixture according to claim 1.